United States Patent [19]

Jackson

[11] 3,996,371
[45] Dec. 7, 1976

[54] OPTIONALLY SUBSTITUTED 3-METHYLSULFINYL INDAZOLES

[75] Inventor: Thomas E. Jackson, Madison, N.J.

[73] Assignee: Sandoz, Inc., E. Hanover, N.J.

[22] Filed: Nov. 17, 1975

[21] Appl. No.: 632,185

[52] U.S. Cl. ............................ 424/273; 260/310 C
[51] Int. Cl.² ............. A61K 31/415; C07D 231/56
[58] Field of Search ................. 424/273; 260/310 C

[56] References Cited

UNITED STATES PATENTS

| | | | |
|---|---|---|---|
| 3,438,992 | 4/1969 | Shen et al. | 260/310 C |
| 3,843,678 | 10/1974 | DiBella | 260/310 C |

FOREIGN PATENTS OR APPLICATIONS

| | | | |
|---|---|---|---|
| 1,277,857 | 9/1968 | Germany | 260/310 C |

OTHER PUBLICATIONS

Chemical Abstracts, vol. 78: 99055s, (1973).

*Primary Examiner*—Donald B. Moyer
*Attorney, Agent, or Firm*—Gerald D. Sharkin; Richard E. Vila; Joseph J. Borovian

[57] ABSTRACT

The invention discloses optionally substituted 3-methylsulfinyl indazoles having pharmacological activity in animals and useful as sleep-inducing agents. The compounds may be prepared by diazotization of an optionally substituted α-methylsulfinyl-o-toluidine.

9 Claims, No Drawings

OPTIONALLY SUBSTITUTED 3-METHYLSULFINYL INDAZOLES

The present invention relates to optionally substituted 3-methylsulfinyl indazoles and to their use as sleep-inducing agents. The invention also relates to pharmaceutical compositions containing the above compounds as an active ingredient thereof and to the method of using such compositions as sleep inducers.

The compounds of this invention may be represented by the following structural formula I:

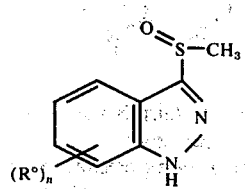

wherein

R° is halo of atomic weight of from 18 to 80 or trifluoromethyl, and $n$ is 0, 1 or 2, provided that when $n$ is 2, R° is halo of atomic weight of from 18 to 80.

The preferred compounds of formula I are those in which R° is trifluoromethyl and $n$ is 1.

The compounds of formula I may be prepared by the following reaction scheme:

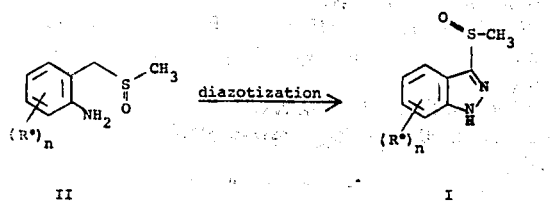

wherein R° and $n$ are as defined above.

The preparation of compounds of formula I involves diazotization of an optionally substituted α-methylsulfinyl-o-toluidine in conventional manner, i.e., by reacting the optionally substituted α-methylsulfinyl-o-toluidine with sodium nitrite and a mineral acid, preferably sulfuric acid. The reaction may be carried out at temperatures in the range of from −35° C. to 40° C., preferably −20° C. to 25° C. Inclusion of a solvent is optional and may be any of those typically employed in diazotization reactions, such as lower alkanols.

The compounds of formula II are either known or can be prepared in conventional manner from available materials, e.g., by the procedures of Claus, Vycudilik and Rieder, Monatsh. Chem. 102, 1571–1582 (1971).

The above-described final compounds may be recovered and refined by conventional techniques, e.g., by crystallization, distillation or chromatographic techniques, e.g., thin-layer or column chromatography, as is appropriate.

The compounds of formula I are useful because they possess pharmacological activity in animals. In particular, the compounds are useful as sleep inducers as indicated: 1) by a reinduction of hexobarbital anesthesia in mice (10–200 mg./kg. i.p.) according to the method of Winter, J. Pharmacol and Exp. Therap. 94, 7–11, 1948; and 2) by scoring for loss of righting reflex according to the method of Reed-Muench (American Journal of Hygiene, 27: 493–497, 1938), in which mice are administered 12.5 mg./kg. i.p. Thioridazine, immediately after which the test compound is administered at dosages of 5 to 200 mg./kg. in a volume of 0.1 ml./10 g. body weight. Sixty minutes after dosing, the mice are scored for loss of righting reflex.

For the above use, the compounds may be combined with one or more pharmaceutically acceptable carriers or adjuvants and may be administered orally in such forms as tablets, capsules, dispersible powders, granules, syrups, elixirs, suspensions, and the like, or parenterally in the forms of sterile injectable solutions or suspensions. These pharmaceutical preparations may contain up to about 90% active ingredient in combination with the carrier or adjuvant. The preferred pharmaceutical compositions from the standpoint of preparation and ease of administration are solid compositions, particularly hard-filled capsules and tablets.

The dosage administered will vary depending upon known variables such as the particular compound, the mode of administration and the severity of the condition being treated. In general, satisfactory results are obtained when the compounds are administered at a daily dosage of from about 5 milligrams to about 200 milligrams per kilogram of animal body weight, typically given orally and in a single dose at bedtime. For most large mammals, the administration of from about 350 milligrams to about 3000 milligrams, preferably 350 to 1500 milligrams, of the compound at bedtime provides satisfactory results.

Tablets and capsules containing the ingredients below may be prepared by conventional techniques and are useful for inducing sleep at a dose of one tablet or capsule at bedtime.

| Ingredients | Weight (mg.) | |
|---|---|---|
| | Tablet | Capsule |
| 3-methylsulfinyl-5-trifluoromethyl indazole | 400 | 400 |
| tragacanth | 10 | — |
| lactose | 247.5 | 300 |
| corn starch | 25 | — |
| talcum | 15 | — |
| magnesium stearate | 2.5 | — |
| | 700 mg | 700 mg. |

The following examples are merely illustrative of specific compounds of the invention and the manner in which they may be prepared.

EXAMPLE 1

3-Methylsulfinyl-5-trifluoromethyl indazole

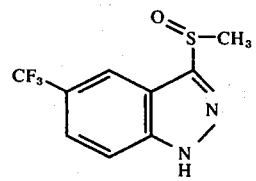

To a cooled (ice/water) solution of 3.7 g. of sodium nitrite predissolved in 20 ml. of water is slowly added 50 ml. of 3N sulfuric acid. To the resulting cooled (ice/water) solution is added dropwise, over a period of 30 minutes, a solution of 12.0 g. of a α-methylsulfinyl-4-trifluoromethyl-o-toluidine predissolved in 200 ml. of 1-propanol, while the temperature is maintained below 10° C. After the reaction mixture is stirred with cooling for an additional 90 minutes, it is allowed to stand overnight at room temperature. The reaction mixture is then nearly concentrated to dryness under vacuum and taken up in 100 ml. of chloroform and 60 ml. of a 15% sodium hydroxide solution. After separation of the phases, the aqueous phase is acidified with concentrated hydrochloric acid and the resulting precipitate filtered off. The acidified aqueous phase is washed three times with chloroform and the combined chloroform extracts are dried over potassium carbonate to a solid. Recrystallization of the crude product from chloroform/hexane yields 3-methylsulfinyl-5-trifluoromethyl indazole, m.p. 168°–170° C.

EXAMPLE 2

Following the procedure of Example 1, but employing appropriate starting materials in approximtely equivalent amounts, the following additional compounds are prepared:

A. 3-methylsulfinyl-4trifluoromethyl indazole,
B. 3-methylsulfinyl-6-trifluoromethyl indazole,
C. 3-methylsulfinyl-7trifluoromethyl indazole,
D. 5-chloro-3-methylsulfinyl indazole, and
E. 4,6-dichloro-3-methylsulfinyl indazole.

What is claimed is:

1. A compound of the formula:

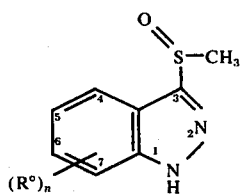

wherein $R°$ is halo of atomic weight of from 18 to 80 or trifluoromethyl, and $n$ is 0, 1 or 2, provided that when $n$ is 2, $R°$ is halo of atomic weight of from 18 to 80.

2. A compound of claim 1 having the formula:

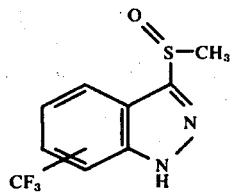

3. The compound of claim 3 which is 3-methylsulfinyl-5-trifluoromethyl indazole.

4. A pharmaceutical composition for inducing sleep in mammals comprising an inert, pharmaceutically acceptable carrier and a sleep-inducing effective amount of a compound of claim 1.

5. The pharmaceutical composition of claim 4 wherein the compound is 3-methylsulfinyl-5-trifluoromethyl indazole.

6. A pharmaceutical composition of claim 4 in unit dosage form an comprise from 350 to 3000 milligrams of the compound.

7. A method of inducing sleep in mammals comprising administering at bedtime to a mammal in need of such treatment a sleep-inducing effective amount of a compound of claim 1.

8. The method of claim 7 wherein the compound administered is 3-methylsulfinyl-5-trifluoromethyl indazole.

9. A method of claim 7 wherein the compound is administered in a daily amount of from 350 to 3000 milligrams.

* * * * *